US00PP37819P2

(12) United States Plant Patent
Mathey

(10) Patent No.: US PP37,819 P2
(45) Date of Patent: Oct. 27, 2026

(54) ***SAMBUCUS* PLANT NAMED 'SMNSNA'**

(50) Latin Name: *Sambucus nigra*
Varietal Denomination: SMNSNA

(71) Applicant: Spring Meadow Nursery Inc, Grand Haven, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/370,939

(22) Filed: Oct. 28, 2025

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
CPC ... A01H 5/12; A01H 5/02; A01H 5/00; A01H 6/00
See application file for complete search history.

(56) References Cited

U.S. PATENT DOCUMENTS

PP15,575 P2 * 2/2005 Tobutt ..... A01H 5/02 Plt./226

* cited by examiner

*Primary Examiner* — June Hwu

(57) ABSTRACT

A new and distinct cultivar of *Sambucus* plant named 'SMNSNA' is disclosed, characterized by dark purple-black mature foliage. Large inflorescences with hot pink flowers give rise to many glossy black fruits. Plants are upright, compact, and flower abundantly. The new cultivar is a *Sambucus*, typically produced as an outdoor ornamental plant.

3 Drawing Sheets

Latin name of the genus and species: *Sambucus nigra.*
Cultivar denomination: 'SMNSNA'.

BACKGROUND OF THE INVENTION

The new cultivar is a product of a planned breeding program conducted by the inventor to produce *Sambucus* cultivars with dark foliage, and new habits and forms. 'SMNSNA' was derived by collecting bulk, open-pollinated seed from a population of unnamed, unpatented *Sambucus nigra* selections. The open pollination resulting in the new cultivar was made in summer 2016 at a nursery in Grand Haven, Michigan.

*Sambucus* 'SMNSNA' was found and selected at the same nursery in Grand Haven, Michigan in summer 2021. The first asexual propagation of 'SMNSNA' was carried out in summer 2021 by softwood cuttings at the same location in Grand Haven, Michigan. Through subsequent propagation, multiple additional generations have been reproduced, having shown that the unique features of this cultivar are stable and reproduced true to type.

SUMMARY OF THE INVENTION

The cultivar 'SMNSNA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNSNA'. These characteristics in combination distinguish 'SMNSNA' as a new and distinct *Sambucus* cultivar:

1. Dark purple-black mature foliage.
2. New growth that is brown with a purple-black tint with some yellow-green especially towards the petiole.
3. Broad, compound leaves (not highly serrate lace-type).
4. Large inflorescences with hot pink flowers that give rise to many glossy black fruits.
5. Abundantly flowering.
6. Upright, compact habit.

PARENTAL COMPARISONS

Parent comparisons are unavailable, as the new cultivar is the result of open pollination.

COMMERCIAL COMPARISONS

'SMNSNA' can be compared to the commercial cultivar *Sambucus nigra* 'Eva', U.S. Plant Pat. No. 15,575. The two *Sambucus* are similar in most horticultural characteristics. The new cultivar, however, differs in the following:

1. Young foliage color of the new cultivar is brown with a purple-black tint with some yellow-green especially towards the petiole, while the young foliage color of this comparator is bright green.
2. Flower color of the new cultivar is hot pink, while the flower color of this comparator is light to medium pink.
3. Leaves of the new cultivar are broad leaf phenotype, while leaves of this comparator are lace leaf prototype.

'SMNSNA' can be compared to the commercial cultivar *Sambucus nigra* 'Thundercloud', unpatented. The two *Sambucus* are similar in most horticultural characteristics. The new cultivar, however, differs in the following:

1. Young foliage color of the new cultivar is brown with a purple-black tint with some yellow-green especially towards the petiole, while the young foliage color of this comparator has less of a purple-black tint.

2. Mature foliage color of the new cultivar is dark purple-black, while the mature foliage color of this comparator is dark but with more bronze undertones.

BRIEF DESCRIPTION OF THE PHOTOGRAPHS

This new *Sambucus* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new hybrid *Sambucus*.

DETAILED BOTANICAL DESCRIPTION

Figure 1:
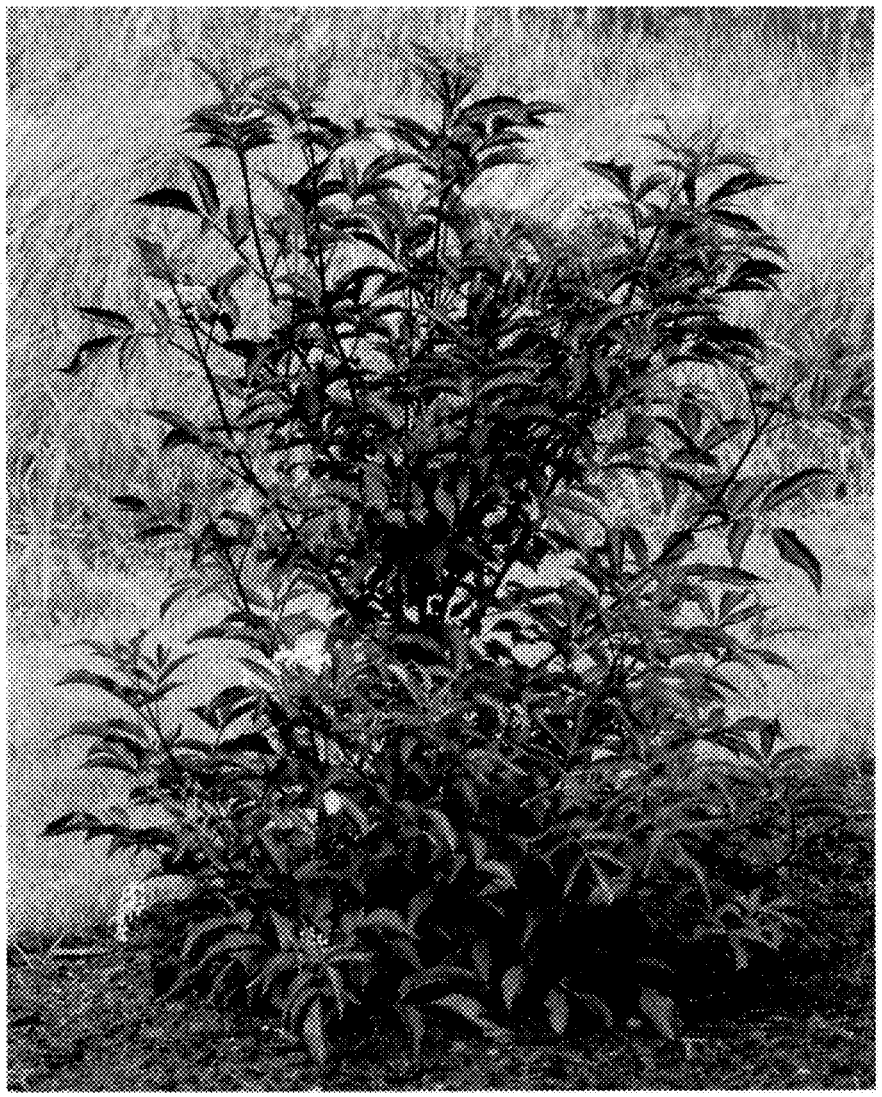
FIG. 1 is a color photograph showing a plant of 'SMNSNA' in Grand Haven, Michigan during early summer with emerging foliage on new stems, mature foliage and developing inflorescences. The plant is approximately 2.5 years old, planted in the ground.
Figure 2:
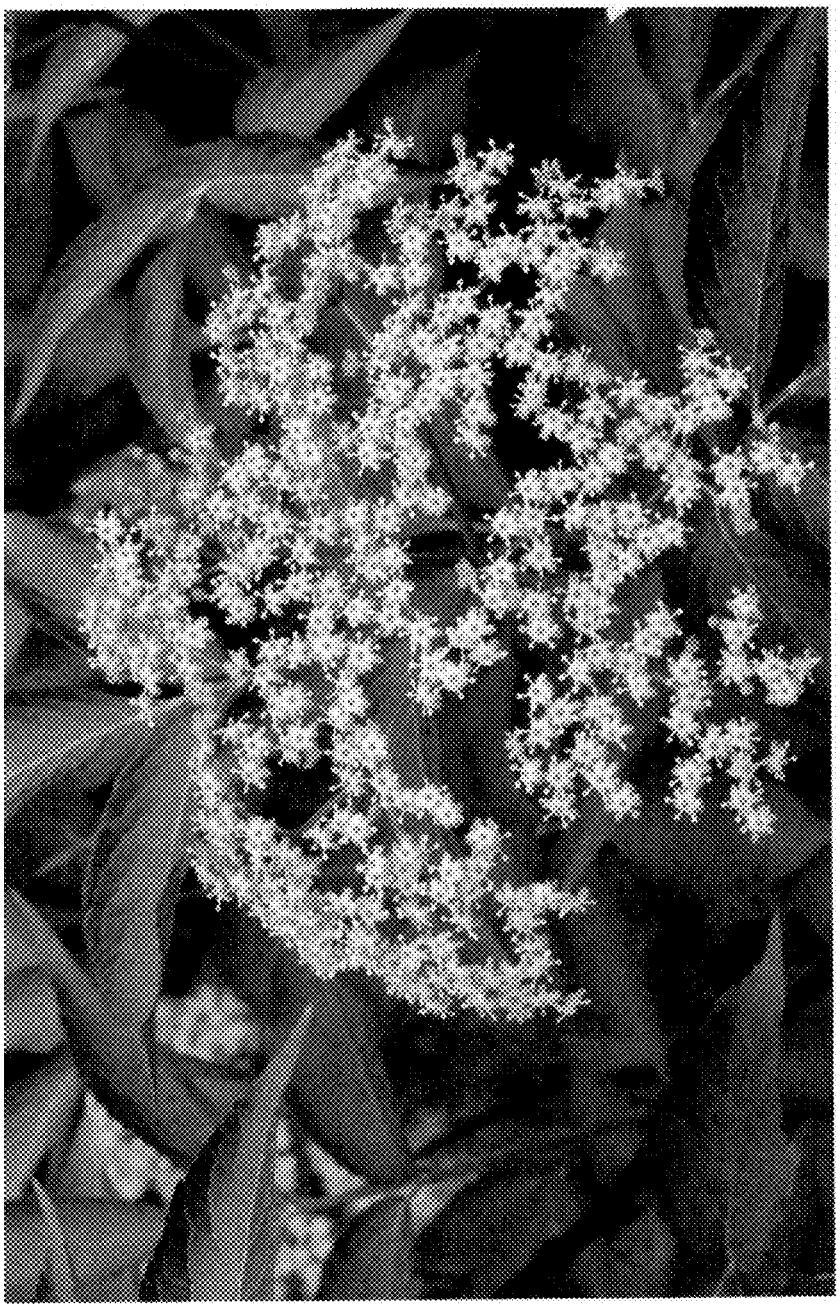
FIG. 2 is a close-up view of an inflorescence and mature foliage of 'SMNSNA'.
Figure 3:
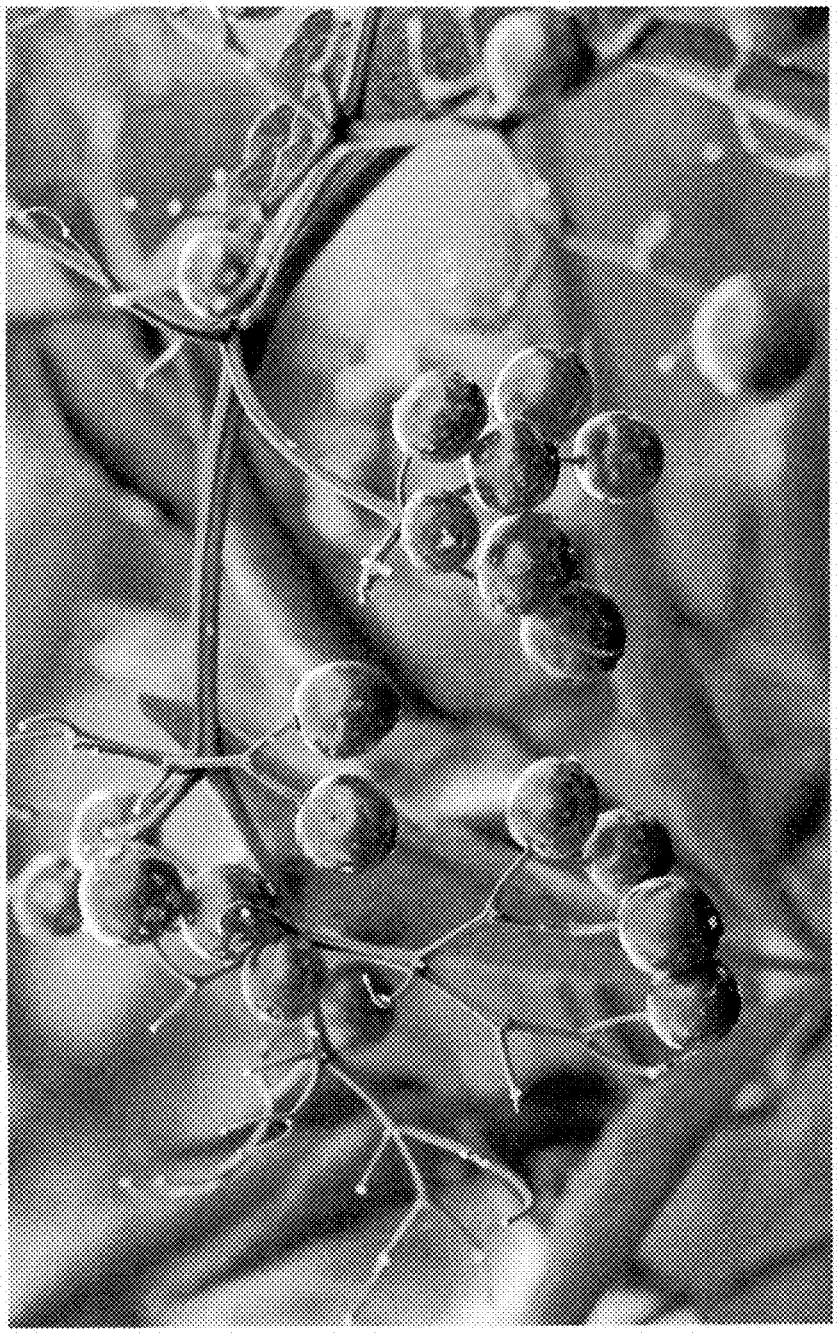
FIG. 3 is a color photograph showing a close-up view of the immature fruits of 'SMNSNA'.

In the following description, color references are made to The Royal Horticultural Society Colour Chart 2015, except where general terms of ordinary dictionary significance are used. The following observations and measurements describe 'SMNSNA' plants grown in a poly-greenhouse in Grand Haven, Michigan. The plants were 3 years old. Temperatures ranged from 5° C. to 10° C. at night to 18° C. to 27° C. during the day. No artificial light, photoperiodic treatments were given to the plants. Measurements and numerical values represent averages of typical plant types. Botanical classification: *Sambucus nigra* 'SMNSNA'.

PROPAGATION

Typical method: Softwood cuttings.
Root initiation: 21 days in summer at approximately 25° C.
Time to produce rooted cutting: About 60 days in summer at approximately 25° C.
Roots: Moderately dense, moderately freely branching, medium thickness, fleshy. White in color, not accurately measured with R.H.S. chart.

PLANT

Plant type: Perennial shrub.
Growth habit: Upright and compact, reaching only about 2-3 feet tall at 3 years.
Shape: Globose to Oval upright.
Height: 65 cm.
Plant spread: 100 cm.
Pot size of plant described: 5 gallon.
Age of plant described: 3 years.
Growth rate: Moderate.
Plant vigor: High.
Stem:
- *Branching*.—Basal.
- *Pinching*.—Some required to encourage well-rounded habit.
- *Number of primary branches*.—6 to 8.
- *Number of secondary branches*.—18 to 20.
- *Shape*.—Rounded.
- *Color*.—Stem: RHS Greyed-Purple 187A to 187B. Bark: Near RHS Brown N200B.
- *Length*.—60 cm.
- *Width*.—4 mm.
- *Aspect*.—0° to 20° from vertical.
- *Strength*.—Moderate to high.
- *Pubescence*.—Slight on new growth only.
- *Internode length*.—14 cm.

Trunk texture: Smooth with protruding lenticels. Lenticels moderately dense, round, about 2 to 4 mm in diameter colored Greyed-Purple N187D.

FOLIAGE

Leaf:
- *Arrangement*.—Opposite.
- *Whole leaf length*.—17 cm.
- *Whole leaf width*.—13 cm.
- *Leaflets per Leaf*.—5 or 7.
- *Leaflet length*.—Terminal: 9 cm. Lateral: 8.5 cm. Base: 6.5 cm.
- *Leaflet width*.—Terminal: 3.75 cm. Lateral: 3 cm. Base: 3 cm.
- *Leaflet shape*.—Terminal: Elliptic. Lateral: Elliptic. Base: Ovate.
- *Leaflet apex*.—Terminal: Acuminate. Lateral: Acuminate. Base: Acuminate.
- *Leaflet base*.—Terminal: Cuneate. Lateral: Cuneate. Base: Rounded.
- *Leaflet margin*.—Serrate.
- *Texture of top surface*.—Glabrous.
- *Texture of bottom surface*.—Glabrous.
- *Color*.—Young Foliage, Upper Side: Near RHS Brown 200A tinted Greyed-Purple 187A and N187A with some Yellow-Green 144B, especially towards petiole. Young Foliage, Under Side: Near RHS Brown 200A tinted Greyed-Purple 187A and N187A with some Yellow-Green 144B, especially towards petiole. Mature Foliage, Upper Side: Near RHS Brown 200A. Mature Foliage, Under Side: Near RHS Grey 201A.

Venation:
- *Type*.—Pinnate.
- *Color*.—Mature, Upper Side: RHS Greyed-Purple 187B. Mature, Under Side: RHS Greyed-Purple 187B.

Petiole:
- *Length*.—8.5 cm.
- *Width*.—3 mm.
- *Petiolule length*.—2 mm.
- *Petiolule width*.—1 mm.
- *Color*.—Upper Side: RHS Greyed-Purple 187A. Under *Side*: RHS Greyed-Purple 187A.
- *Texture*.—Upper Side: Glabrous. Under Side: Glabrous.
- *Strength*.—Medium.

INFLORESCENCE

Natural flowering season: Early summer (May-June).
Flower arrangement: Inflorescence.
Flowering habit: Terminal.
Inflorescence type: Compound umbel.

Height: 6 cm.
Diameter: 20 cm.
Quantity of flowers per inflorescence: About 500.
Quantity of inflorescences per lateral stem: 1.
Quantity of flowers per plant: About 5,000.
Quantity of buds per plant: About 2,000.
Quantity of flowers and buds per plant: About 7,000.
Fragrance: Slightly floral with musky undertones; mild to moderate.
Flower:
*Type or form*.—Rotate.
*Density of flower coverage over plant*.—Moderate.
*Aspect*.—Upright.
*Length*.—3 mm.
*Diameter*.—5 mm.
*Depth*.—5 mm.
*Persistence*.—Self-cleaning.
Bud:
*Length*.—1.5 mm.
*Diameter*.—1.5 mm.
*Shape*.—Globose.
*Color*.—RHS Greyed-Purple 187A.
*Texture*.—Glabrous.
*Luster*.—Matte.
Petals:
*Number*.—5.
*Arrangement*.—Stellate, single whorl.
*Shape*.—Broadly elliptic.
*Tip*.—Rounded.
*Base*.—Fused.
*Margin*.—Entire.
*Length*.—2 mm.
*Width*.—1.5 mm.
*Texture*.—Upper side: Glabrous, silky. Under side: Glabrous, silky.
*Color*.—When Opening, Upper Side: RHS Red-Purple 72A with Red-Purple 73D at the base. When Opening, Under Side: RHS Red-Purple 72A. Fully Opened, Upper Side: RHS Red-Purple 72A with Red-Purple 73D at the base. Fully Opened, Under Side: RHS Red-Purple 72A.
Sepals:
*Number*.—5.
*Arrangement*.—Whorl; stellate; single whorl.
*Shape*.—Narrowly elliptic.
*Tip*.—Acute.
*Base*.—Fused.
*Margin*.—Entire.
*Length*.—0.5 mm.
*Width*.—0.5 mm.
*Texture*.—Upper side: Glabrous. Under side: Glabrous.
*Luster*.—Upper side: Matte. Under side: Matte.
*Color*.—When Opening, Upper Side: RHS Red-Purple 72A. When Opening, Under Side: RHS Red-Purple 72A. Mature, Upper Side: RHS Red-Purple 72A. Mature, Under Side: RHS Red-Purple 72A.
Calyx:
*Shape*.—Collar-like.
*Length*.—2 mm.
*Diameter*.—2 mm.
Peduncle:
*Terminal length*.—9 cm.
*Terminal diameter*.—3 mm.
*Angle*.—0° from vertical.
*Strength*.—Moderate.
*Texture*.—Glabrous.
*Color*.—RHS Greyed-Purple 187A.

REPRODUCTIVE ORGANS

Stamens:
*Number*.—5.
*Filament length*.—2 mm.
*Filament color*.—RHS White 155A.
Anthers:
*Shape*.—Oblong.
*Length*.—1 mm.
*Width*.—0.5 mm.
*Color*.—RHS Greyed-Red 180B to 180C.
*Pollen amount*.—Abundant.
*Pollen color*.—RHS Yellow 10B.
Pistil:
*Number*.—1.
*Length*.—1 mm.
Stigma:
*Shape*.—Peltate.
*Color*.—RHS Red-Purple 72A.
*Diameter*.—1 mm.
*Style length*.—Less than 1 mm.
*Style color*.—RHS Red-Purple 72A.

SEEDS

*Quantity*.—3 per flower.
*Length*.—4 mm.
*Width*.—2 mm.
*Color*.—RHS Greyed-Orange 164C.

FRUIT

*Quantity per branch*.—Several hundred.
*Quantity per plant*.—Several thousand.
*Length*.—6 mm.
*Width*.—5 mm.
*Shape*.—Round.
*Color*.—Skin: Immature color: RHS Greyed-Purple 187A flushed 187C. Mature color: RHS Brown 200A and Black 203B. Flesh: RHS Green NN137B.
*Luster*.—Glossy.
*Texture*.—Smooth-skinned.
*Taste*.—Fruits are edible if cooked.

OTHER CHARACTERISTICS

Fruit and seed: Not observed to date.
Disease and insect resistance: Neither resistance nor susceptibility to normal diseases and pests of *Sambucus* have been observed.
Temperature tolerance: Hardy in USDA Zones 4 to 8.

What is claimed is:

1. A new and distinct cultivar of *Sambucus* plant named 'SMNSNA' as herein illustrated and described.

* * * * *